United States Patent
Chen et al.

(10) Patent No.: US 7,087,556 B2
(45) Date of Patent: *Aug. 8, 2006

(54) COMPOSITIONS FOR TREATING SUBTERRANEAN ZONES PENETRATED BY WELL BORES

(75) Inventors: Shih-Ruey T. Chen, Pittsburgh, PA (US); Jiten Chatterji, Duncan, OK (US); Valentino L. DeVito, Pittsburgh, PA (US); Randy J. Loeffler, Carnegie, PA (US); Kevin W. Frederick, Evans City, PA (US); Kevin W. Smith, McMurray, PA (US)

(73) Assignee: WSP Chemicals & Technology, L.L.C., Ambridge, PA (US)

(*) Notice: Subject to any disclaimer, the term of this patent is extended or adjusted under 35 U.S.C. 154(b) by 468 days.

This patent is subject to a terminal disclaimer.

(21) Appl. No.: 10/122,869

(22) Filed: Apr. 15, 2002

(65) Prior Publication Data

US 2003/0008779 A1    Jan. 9, 2003

Related U.S. Application Data

(60) Provisional application No. 60/284,043, filed on Apr. 16, 2001.

(51) Int. Cl.
 *C09K 8/35* (2006.01)
 *C09K 8/40* (2006.01)
 *C09K 8/94* (2006.01)
(52) U.S. Cl. ............... 507/216; 507/102; 507/202; 507/114; 507/121; 507/226; 507/140; 507/269; 526/286; 526/287; 526/288
(58) Field of Classification Search ............ 507/102, 507/202, 114, 121, 216, 226, 140, 269; 526/286, 526/287, 288
 See application file for complete search history.

(56) References Cited

U.S. PATENT DOCUMENTS

| | | | |
|---|---|---|---|
| 3,513,120 A * | 5/1970 | Pohlemann et. al. ........ 524/460 |
| 3,563,963 A * | 2/1971 | Beier .......................... 526/93 |
| 3,770,673 A | 11/1973 | Slagel et al. |
| 4,015,991 A | 4/1977 | Persinski et al. |
| 4,028,290 A | 6/1977 | Reid |
| 4,105,605 A | 8/1978 | Cottrell et al. |
| 4,107,057 A | 8/1978 | Dill et al. |
| 4,460,627 A | 7/1984 | Weaver et al. |
| 4,464,523 A | 8/1984 | Neigel et al. |
| 4,500,357 A | 2/1985 | Brothers et al. |
| 4,515,635 A | 5/1985 | Rao et al. |
| 4,532,052 A | 7/1985 | Weaver et al. |
| 4,540,510 A | 9/1985 | Karl |
| 4,555,269 A | 11/1985 | Rao et al. |
| 4,557,763 A | 12/1985 | George et al. |
| 4,622,373 A | 11/1986 | Bardoliwalla |
| 4,640,942 A * | 2/1987 | Brothers ..................... 523/130 |
| 4,676,317 A | 6/1987 | Fry et al. |
| 4,678,591 A | 7/1987 | Giddings et al. |
| 4,687,516 A | 8/1987 | Burkhalter et al. |
| 4,699,225 A | 10/1987 | Bardoliwalla |
| 4,703,801 A | 11/1987 | Fry et al. |
| 5,049,288 A | 9/1991 | Brothers et al. |
| 5,134,215 A | 7/1992 | Huddleston et al. |
| 5,147,964 A | 9/1992 | Huddleston et al. |
| 5,151,131 A | 9/1992 | Burkhalter et al. |
| 5,263,542 A | 11/1993 | Brothers |
| 5,264,470 A | 11/1993 | Eoff |
| 5,273,580 A | 12/1993 | Totten et al. |
| 5,295,543 A | 3/1994 | Terry et al. |
| 5,298,070 A | 3/1994 | Cowan |
| 5,327,968 A | 7/1994 | Onan et al. |
| 5,332,041 A | 7/1994 | Onan et al. |
| 5,340,397 A | 8/1994 | Brothers |
| 5,346,012 A | 9/1994 | Heathman et al. |
| 5,346,550 A | 9/1994 | Kunzi et al. |
| 5,355,954 A | 10/1994 | Onan et al. |
| 5,355,955 A | 10/1994 | Rodrigues et al. |
| 5,389,706 A | 2/1995 | Heathman et al. |
| 5,398,758 A | 3/1995 | Onan et al. |
| 5,398,759 A | 3/1995 | Rodrigues et al. |
| 5,421,881 A | 6/1995 | Rodrigues et al. |
| 5,447,198 A | 9/1995 | Kunzi et al. |
| 5,458,195 A | 10/1995 | Totten et al. |
| 5,536,311 A | 7/1996 | Rodrigues |
| 5,569,324 A | 10/1996 | Totten et al. |
| 5,571,318 A | 11/1996 | Griffith et al. |
| 5,866,517 A | 2/1999 | Carpenter et al. |
| 5,945,387 A | 8/1999 | Chatterji |
| 5,968,879 A | 10/1999 | Onan et al. |
| 5,985,801 A | 11/1999 | Hoff |
| 6,012,524 A | 1/2000 | Chatterji et al. |
| 6,089,318 A | 7/2000 | Laramay et al. |
| 6,124,244 A * | 9/2000 | Murphey ..................... 507/111 |
| 6,124,245 A * | 9/2000 | Patel ........................... 507/120 |
| 6,171,386 B1 | 1/2001 | Sabins |
| 6,235,809 B1 | 5/2001 | DiLullo Arias et al. |

(Continued)

*Primary Examiner*—Philip C. Tucker
(74) *Attorney, Agent, or Firm*—Gary Matz; Blynn L. Shideler; BLK Law Group

(57) ABSTRACT

The present invention provides compositions of treating subterranean zones penetrated by well bores in primary well cementing operations, well completion operations, production stimulation treatments and the like. The invention includes aqueous well treating fluids comprised of water and a water soluble polymer complex fluid loss control additive. Preferred polymer complexes comprise water-soluble polymers made in the presence of hydroxyethylcellulose.

19 Claims, No Drawings

U.S. PATENT DOCUMENTS

| | | |
|---|---|---|
| 6,242,540 B1 * | 6/2001 | Crevecoeur et al. .......... 526/73 |
| 6,244,344 B1 | 6/2001 | Chatterji et al. |
| 6,268,406 B1 | 7/2001 | Chatterji et al. |
| 6,350,309 B1 | 2/2002 | Chatterji et al. |
| 6,590,050 B1 * | 7/2003 | Bair et al. .................. 526/240 |

* cited by examiner

COMPOSITIONS FOR TREATING SUBTERRANEAN ZONES PENETRATED BY WELL BORES

CROSS-REFERENCES TO RELATED APPLICATIONS

This application claims the benefit of U.S. Provisional Application 60/284,043 entitled "Water Soluble Polymer Complexes" filed on Apr. 16, 2001

BACKGROUND OF THE INVENTION

1. Field of the Invention

The present invention relates to compositions for treating subterranean zones penetrated by well bores. The compositions include polymer complexes and aqueous treating fluids comprised of water and a water soluble fluid loss additive comprised of a polymer complex.

2. Description of the Prior Art

Well treating fluids are used in a variety of operations and treatments in oil and gas wells. Such operations and treatments include well completion operations such as gravel packing to prevent formation solids from being carried out of the well bore with produced hydrocarbon fluids. In gravel packing, suspended gravel particles are carried into a subterranean zone containing a screen in which a gravel pack is to be placed by a viscous gelled treating fluid. Once the gravel pack is placed in the zone, the viscous gelled fluid is broken (the viscosity is reduced) and recovered (returned to the surface). In order to prevent the loss of fluid components of the treating fluid into permeable formations penetrated by the well bore, a fluid loss control additive is included in the treating fluid. The gravel pack formed in the well bore functions as a filter to separate formation solids from produced fluids while permitting the produced fluids to flow into and through the well bore.

Aqueous well treating fluids containing hydraulic cement are utilized extensively in the construction and repair of oil and gas wells. For example, hydraulic cement compositions are used in primary well cementing operations which involve the placement of a cement composition into the annular space between the walls of a well bore and the exterior surfaces of a pipe string such as casing disposed therein. The cement composition is permitted to set in the annular space thereby forming an annular sheath of hardened impermeable cement therein. The objective of the cement sheath is to physically support and position the pipe string in the well bore and bond the pipe string to the walls of the well bore whereby the undesirable migration of formation fluids between subterranean zones penetrated by the well bore is prevented.

An example of a production stimulation treatment utilizing a well treating fluid is hydraulic fracturing. That is, a viscous gelled aqueous treating fluid, referred to in the art as a fracturing fluid, is pumped through the well bore into a subterranean zone to be stimulated at a rate and pressure such that fractures are formed and extended into the subterranean zone. The fracturing fluid also carries particulate proppant material, e.g., sand, into the fractures. The proppant material is suspended in the viscous fracturing fluid so that the proppant material is deposited in the fractures when the viscous fracturing fluid is broken and recovered. The proppant material functions to prevent the formed fractures from closing whereby conductive channels are formed through which production fluids can flow to the well bore. In order to prevent the loss of the fracturing fluid to permeable subterranean formations, a water soluble fluid loss control additive is included in the fracturing fluid. After the viscous fracturing fluid has been pumped into a subterranean zone in a formation and fracturing of the zone has taken place, the fracturing fluid is removed from the formation to allow produced hydrocarbons to flow through the created fractures. Generally, the removal of the viscous fracturing fluid is accomplished by converting the fracturing fluid into a low viscosity fluid. This is accomplished by adding a delayed breaker, i.e., a viscosity reducing additive, to the fracturing fluid prior to pumping it into the subterranean zone to be fractured.

The success of gravel packing operations, primary cementing operations, fracturing operations and other operations utilizing aqueous well treating fluids depends, at least in part, on the ability of the treating fluid used to retain water until it has been placed in a desired well location. That is, as an aqueous treating fluid is pumped through the well bore and contacts permeable subterranean formations penetrated thereby, water included in the treating fluid can be lost to the permeable formations. The loss of water from the treating fluid can prevent the treating fluid from functioning in the manner intended. For example, when portions of the water forming a cement composition are lost, the consistency of the cement composition is also lost which can prevent the composition from being placed in the intended location, the composition can become too viscous for placement and/or the composition fractures subterranean formations whereby all or part of the composition is lost. While lightweight foamed aqueous treating fluids such as foamed cement compositions are often utilized, such foamed treating fluids are also subject to fluid loss when in contact with permeable surfaces.

Heretofore, a variety of fluid loss reducing additives have been developed and used in aqueous well treating fluids. Such additives reduce the loss of liquids, usually water, from such treating fluids when the treating fluids are in contact with permeable surfaces. While the heretofore utilized fluid loss control additives have achieved varying degrees of success, there is a continuing need for improved fluid loss control additives which can be utilized in non-foamed and foamed aqueous well treating fluids and which effectively reduce fluid loss from the aqueous well treating fluids at high temperatures.

SUMMARY OF THE INVENTION

The present invention provides improved compositions for treating subterranean zones penetrated by well bores. The compositions include aqueous well treating fluids having improved low fluid loss properties which meet the needs described above and overcome the shortcomings of the prior art. Further, the compositions comprise interjacent polymer complexes as described herein.

The improved compositions of this invention for treating a subterranean zone penetrated by a well bore comprise aqueous well treating fluids comprised of water and a water soluble polymer complex fluid loss control additive. The fluid loss control additive is comprised of a polymer complex of two or more water-soluble polymers. That is, the fluid loss control additives of this invention are polymer complexes comprised of a cationic, anionic or amphoteric polymer formed in the presence of a nonionic polymer. The polymer complexes are comprised of polymers which are not physically (mechanically) blended, but which are intimately intermixed or interjacent because of the way they are produced. The fluid loss control additive polymer complexes are produced by forming one of the polymeric components in the presence of another polymeric component which is already in place in the polymerization zone. Thus, a solution, emulsion or other preparation of the monomers desired to be incorporated in the formed polymer is prepared with the desired initiator or catalyst and a polymer is formed (synthesized) in the presence of a previously prepared or natural polymer, which is herein referred to as the host polymer. Because the host polymer is present throughout the polymerization mix, the newly formed polymer is interjacent with the host polymer, and for convenience we may refer to the newly synthesized polymer as the intercalated polymer. Since both the polymers of the polymer complex formed are water soluble, the polymer complex is water soluble.

The nonionic polymer, i.e., the host polymer, in the fluid loss control additive of the present invention is preferably a natural polymer. More preferably, the nonionic polymer is a hydroxyalkylated natural gum, and most preferably, the nonionic polymer is ethoxylated hydroxyethylcellulose. The cationic, anionic or amphoteric polymer (the intercalated polymer) which is polymerized in the presence of the nonionic (host) polymer is preferably comprised, at least in part, of monomer units derived from a sulfonic acid functional monomer. Most preferably, the polymer is comprised of 2-acrylamido-2-methyl propane sulfonic acid monomer units which are present in the polymer in an amount in the range of from about 25 mole % to about 75 mole %. The intercalated polymer can include other monomer units such as N,N-dimethylacrylamide, acrylamide, acrylic acid and vinylpyrrolidone.

A preferred composition of this invention for treating a subterranean zone penetrated by a well bore comprises an aqueous well treating fluid comprised of water and a water soluble polymer complex fluid loss control additive comprised of 1 part by weight of a polymer comprising 70 mole % of 2-acrylamido-2-methyl propane sulfonic acid (AMPS), 17 mole % of N,N-dimethylacrylamide (NNDMA) and 13 mole % of acrylamide (AM), and 2 parts by weight hydroxyethylcellulose having 1.5 moles of ethylene oxide substitution. One need not follow these proportions precisely, and accordingly it may be said that the host polymer (hydroxyethylcellulose having 1–2 moles of ethylene oxide substitution) may be present in a ratio of 1.5–2.5 parts by weight to 1 part by weight of intercalated polymer, which contains the monomers recited in molar ratios of 62–78 AMPS:14–20 NNDMA:10–16 AM.

Another preferred water soluble polymer complex fluid loss control additive for use in accordance with the methods of this invention is comprised of 1 part by weight of a polymer comprising 40 mole % of 2-acrylamido-2-methyl propane sulfonic acid 30 mole % of acrylamide, 20 mole % of acrylic acid (AA) and 10 mole % of vinylpyrrolidone (VP), and 1 part by weight of hydroxyethylcellulose having 1.5 moles of ethylene oxide substitution. Again, one need not utilize these proportions precisely, and accordingly it may be said that the host polymer (hydroxyethylcellulose having 1–2 moles of ethylene oxide substitution) may be present in a ratio of 0.5–1.5 parts by weight to 1 part by weight of intercalated polymer, which contains the monomers recited in molar ratios of 32–48 AMPS:25–35 AM:16–24 AA:7–13 VP.

The aqueous well treating fluid can be a foamed or non-foamed hydraulic cement composition, a viscous gravel pack forming fluid, a fracturing fluid or other aqueous well treating fluid.

The objects, features and advantages of this invention will be readily apparent to those skilled in the art upon a reading of the description of preferred embodiments which follows.

DESCRIPTION OF PREFERRED EMBODIMENTS

The present invention provides improved compositions for treating subterranean zones penetrated by well bores including fluids containing water soluble polymer complex fluid loss control additives. That is, the treating fluids are basically comprised of water and a novel polymer complex fluid loss control additive and may include hydraulic cement, viscosity increasing gelling agents, cross-linkers for the gelling agents, viscosity breakers and other components known to those skilled in the art. Thus, the treating fluids useful in accordance with the methods of this invention can be compositions basically comprised of water and the polymer complex fluid loss control additive, hydraulic cement compositions, gravel pack forming compositions, fracturing fluids and the like. When the treating fluid is comprised of water and the fluid loss control additive, the fluid loss control additive is present in an amount in the range of from about 0.09% to about 2.5% by weight of the water. The polymer complex itself is included in the invention.

The water soluble polymer complex fluid loss control additives useful in accordance with this invention are comprised of a complex of two water soluble polymers. The polymer complexes are prepared by polymerizing one or more polymerizable monomers in the presence of a previously formed or natural polymer. The polymer complexes are intercalated as a result of the way they are produced. That is, the complexes are prepared by polymerizing monomer components in the presence of a previously formed or natural polymer which is included in the polymerization mixture. A solution, emulsion or other preparation of the monomers to be polymerized is prepared with the desired initiator or catalyst and a polymer is synthesized in the presence of the previously formed or natural polymer, i.e., the host polymer. Because the host polymer is present throughout the polymerization mixture, the host polymer is intercalated with the new polymer being formed. Both of the polymers are water soluble which makes the polymer complex water soluble. In oil and gas well completion and production stimulation applications, the polymer complex fluid loss control additives are preferably formed by polymerizing a cationic, anionic or amphoteric polymer in the presence of a nonionic host polymer.

As mentioned above, the polymer complex fluid loss control additives are particularly suitable for use in treating fluids which are basically comprised of water and other components such as hydraulic cement, viscosity increasing gelling agents or the like. Stated another way, the polymer complex fluid loss control additives are particularly suitable for use in aqueous well treating fluids such as foamed or nonfoamed hydraulic cement compositions, viscous aqueous fracturing fluids and other aqueous well treating fluids utilized in the drilling, completion and stimulation of oil and gas wells.

The polymer complex fluid loss control additives useful in accordance with this invention are particularly suitable for use in foamed or nonfoamed hydraulic cement compositions which are utilized for cementing well bores at high temperatures, i.e., temperatures in the range of from about 80° F. to the bottom hole circulation temperature (BHCT), i.e., about 350° F. The polymer complexes provide fluid loss control over a wide range of temperature and other well conditions.

As mentioned, the polymer complexes of the present invention are formed by polymerizing one or more monomers in the presence of a host polymer. The host polymer can be a synthetic polymer such as those produced by free radical polymerization or condensation polymerization or it may be a natural polymer such as a natural gum, a starch, a modified starch, a cellulosic material or a modified cellulosic material. Examples of host polymers that can be utilized in the polymer complex include, but are not limited to, water-soluble vinyl polymers, polyolefins, polyacrylates, polyamides, polyesters, polyurethanes, xanthan gums, sodium alginates, galactomannans, carragenan, gum arabic, cellulose and its derivatives, starch and its derivatives, guar and its derivatives, silicone containing polymers and their derivatives, polysiloxanes and their derivatives and proteins and their derivatives.

The host polymer is preferably a nonionic polymer such as a water soluble natural gum. While various natural gums can be used of the types described above, a hydroxyalkylated natural gum such as hydroxyethylcellulose with or without ethylene oxide substitution is preferred. As is known in the art, hydroxycellulose may be ethoxylated at one or more of the three available sites on each glucose unit of the hydroxycellulose, substituting one or more ethoxy groups at each site. As used herein and conventionally, the term "hydroxyethylcellulose having 1–2 moles of ethylene oxide substitution" and similar terms such as "hydroxyethylcellulose having 1.5 moles of ethylene oxide substitution" mean to relate the ethylene oxide substitution to a molar unit derived from glucose in the hydroxycellulose. We prefer to use hydroxyethyl cellulose having 1.4–1.6 moles of ethylene oxide substitution.

The cationic, anionic or amphoteric polymer formed in the presence of the nonionic host polymer can include monomer units derived from one or more monomers. Preferably, a majority of the monomer units for forming the polymer are monomer units derived from a sulfonic acid functional monomer. Of the various sulfonic acid functional monomers that can be used, 2-acrylamido-2-methyl propane sulfonic acid monomer units present in the polymer in an amount in the range of from about 25 mole % to about 75 mole % are preferred. One or more additional monomer units can be included in the formed polymer in addition to the sulfonic acid functional monomer units. Preferred such additional monomer units are N,N-dimethylacrylamide monomer units present in the polymer in an amount in the range of from about 10 mole % to about 40 mole %, acrylamide monomer units present in the polymer in an amount in the range of from about 10 mole % to about 30 mole %, acrylic acid monomer units present in the polymer in an amount in the range of from about 10 mole % to about 20 mole % and/or vinylpyrrolidone monomer units present in the polymer in an amount in the range of from about 5 mole % to about 20 mole %. Preferably, the weight ratio of the cationic, anionic or amphoteric polymer to the nonionic polymer is in the range of from about 1:10 to about 10:1. Other useful ranges include 100:1 to 1:100, 75:1 to 1:75, 25:1 to 1:25, 5:1 to 1:5, and 2:1 to 1:2 by weight.

A particularly suitable water soluble polymer complex fluid loss control additive for use in accordance with this invention is comprised of 1 part by weight of a polymer comprised of about 70 mole % of 2-acrylamido-2-methyl propane sulfonic acid, about 17 mole % of N,N-dimethylacrylamide and about 13 mole % of acrylamide, and 2 parts by weight of hydroxyethylcellulose having 1.5 moles of ethylene oxide substitution.

Another particularly preferred water soluble polymer complex fluid loss control additive for use in accordance with this invention is comprised of 1 part by weight of a polymer comprised of about 40 mole % of 2-acrylamido-2-methyl propane sulfonic acid, about 30 mole % of acrylamide, about 20 mole % of acrylic acid and about 10 mole % of vinyl pyrrolidone, and 1 part by weight of hydroxyethylcellulose having 1.5 moles of ethylene oxide substitution.

A composition of this invention for cementing a subterranean zone penetrated by a well bore comprises a cement composition comprised of a hydraulic cement slurried with water present in an amount in the range of from about 35% to about 50% by weight of cement in the composition and a water soluble polymer complex fluid loss control additive present in an amount in the range of from about 0.25% to about 5% by weight of cement in the composition.

Another composition of this invention for cementing a subterranean zone penetrated by a well bore comprises a cement composition comprised of a hydraulic cement slurried with water present in an amount in the range of from about 35% to about 50% by weight of cement in the composition, a water soluble polymer complex fluid loss control additive present in an amount in the range of from about 0.25% to about 5% by weight of cement in the composition, a gas present in an amount sufficient to foam the aqueous well treating fluid and a mixture of foaming and foam stabilizing surfactants present in an effective amount.

A variety of hydraulic cements can be utilized in accordance with the present invention including those comprised of calcium, aluminum, silicon, oxygen and/or sulfur which set and harden by reaction with water. Such hydraulic cements include, but are not limited to, Portland cements, pozzolana cements, gypsum cements, aluminous cements, silica cements, and slag cements. Portland cements are generally preferred for use in accordance with this invention. Portland cements of the types defined and described in *API Specification For Materials And Testing For Well Cements*, API Specification 10, $5^{th}$ Edition, dated Jul. 1, 1990 of the American Petroleum Institute are particularly suitable. Preferred such API Portland cements include classes A, B, C, G and H, with API classes G and H being more preferred and class H being the most preferred.

The water utilized in a cement composition of this invention is present in a quantity sufficient to produce a pumpable slurry of desired density. The water can be fresh water or salt water. The term "salt water" is used herein to mean unsaturated salt solutions and saturated salt solutions including brines and seawater. The water is generally present in the cement compositions in an amount in the range of from about 35% to about 50% by weight of the cement in the composition.

As mentioned above, the polymer complex fluid loss control additive is preferably made by forming a cationic, anionic or amphoteric polymer in the presence of a host nonionic polymer. Such polymer complexes provide excellent fluid loss control in both nonfoamed and foamed cement compositions over a wide range of temperature and well conditions. When the polymer complex includes a formed polymer or a host polymer of one or more acrylamide type monomers and/or a basic vinylheterocyclic monomer such as vinylimidazole, vinylpyridine, vinylpyrrolidone and their derivatives, the cementing composition may optionally include a dispersant such as naphthalene sulfonic acid condensed with formaldehyde or the condensation reaction product of acetone, formaldehyde and sodium bisulfite which can be a part of the polymer complex. The inclusion of monomer units of a dispersant has a synergistic affect on the polymer complex which results in an unexpected increase in its effectiveness as a fluid loss control additive.

When included, the dispersant monomer units are present in the cationic, anionic or amphoteric polymer in an amount in the range of from about 0.5 mole % to a maximum about 2 mole %.

The various additives conventionally included in cement compositions which are well known to those skilled in the art can also be utilized in the cement compositions of this invention in amounts known to those skilled in the art.

The polymer complex fluid loss control additives of this invention, when used in a cement composition, effect a substantial reduction in the rate of water loss from the cement composition as well as in the apparent viscosity of the cement composition. The polymer complex is easily mixed with the other components of the cement composition and results in good fluid loss control over a wide temperature range without affecting rheology adversely. The polymer complex can be added to a cement composition in dry, solution or emulsion form. The presence of the polymer complex fluid loss control additive in a cement composition also improves the pumpability of the cement composition, improves drilling fluid removal and reduces the possibility of lost circulation in primary cementing applications.

As mentioned above, the polymer complex fluid loss control additive included in a cement composition of this invention is preferably selected from the group of a polymer complex comprised of 1 part by weight of a polymer comprising 70 mole % of 2-acrylamido-2-methyl propane sulfonic acid, 17 mole % of N,N-dimethylacrylamide and 13 mole % of acrylamide, and 2 parts by weight of hydroxyethylcellulose containing 1.5 moles of ethylene oxide substitution; or a polymer complex comprised of 1 part by weight of a polymer comprising 40 mole % of 2-acrylamido-2-methyl propane sulfonic acid, 30 mole % of acrylamide, 20 mole % of acrylic acid and 10 mole % of vinylpyrrolidone, and 1 part by weight of hydroxyethylcellulose having 1.5 moles of ethylene oxide substitution.

The polymer complex fluid loss control additive utilized is included in the cement composition in an amount in the range of from about 0.25% to about 5% by weight of cement in the cement composition.

When the cement composition is foamed, a gas in an amount sufficient to foam the cement composition and a mixture of foaming and foam stabilizing surfactants present in an effective amount are included in the cement composition. The gas utilized for forming the foamed cement composition can be air or nitrogen, with nitrogen being preferred.

The gas is generally present in the cement composition in an amount in the range of from about 10% to about 80% by volume of the final foamed cement composition.

While various mixtures of foaming and foam stabilizing surfactants can be utilized, a particularly suitable and preferred such mixture is comprised of an ethoxylated alcohol ether sulfate surfactant, an alkyl or alkene amidopropyl betaine surfactant and an alkyl or alkene amidopropyldimethylamine oxide surfactant. This surfactant mixture is described in detail in U.S. Pat. No. 6,063,738 issued to Chatterji et al. on May 16, 2000, the disclosure of which is incorporated herein by reference thereto.

The mixture of foaming and foam stabilizing surfactants is present in the cement composition in an effective amount, i.e., in an amount in the range of from about 0.8% to about 5% by volume of water in the cement composition.

Another aqueous well treating fluid which can be utilized in accordance with the methods of this invention is comprised of water, a gelling agent present in an amount in the range of from about 0.125% to about 1.5% by weight of water in the aqueous well treating fluid and a water soluble polymer complex fluid loss control additive present in an amount in the range of from about 0.1% to about 5% by weight of water in the aqueous well treating fluid.

The water utilized in the well treating fluid can be fresh water or salt water as described above.

One or more gelling agents for increasing the viscosity of the aqueous treating fluid are included therein. The increased viscosity of the treating fluid allows the treating fluid to carry particulate solid materials and deposit the particulate solid materials in a desired location. For example, when the viscous gelled aqueous treating fluid is utilized as a fracturing fluid, it is pumped into a subterranean zone by way of the well bore at a rate and pressure sufficient to fracture the subterranean zone. The viscous fracturing fluid carries particulate proppant material such as graded sand into the fractures. The proppant material is suspended in the viscous fracturing fluid so that the proppant material is deposited in the fractures when the viscous fracturing fluid is broken (reverts to a thin fluid) and recovered. The proppant material functions to prevent the fractures from closing whereby conductive channels are formed through which produced fluids can flow to the well bore.

A viscous gelled aqueous treating fluid is also utilized in gravel packing. In gravel packing operations, solid gravel particles, such as graded sand or the like, are carried into a subterranean zone containing a screen within which a gravel pack is to be placed by the viscous aqueous treating fluid. That is, the gravel is suspended in the viscous aqueous treating fluid at the surface and carried into a space between the screen and the walls of the well bore penetrating the subterranean zone within which the gravel pack is to be placed. Once the gravel is placed in the zone, the viscous gelled fluid is broken (the viscosity is reduced) and recovered (returned to the surface). The gravel pack functions as a filter to separate formation solids from produced fluids while permitting the produced fluids to flow into and through the well bore.

A variety of gelling agents can be utilized to increase the viscosity of aqueous well treating fluids such as fracturing fluids, gravel packing fluids and the like. The useful gelling agents include natural and derivatized polysaccharides which are soluble, dispersible or swellable in an aqueous liquid to yield viscosity to the liquid. One group, for example, of polysaccharides which are suitable for use in accordance with the present invention includes, but is not limited to, galactomannan gums such as gum arabic, gum ghatti, gum karaya, tamarind gum, tragacanth gum, guar gum, locust bean gum, and the like. The gums can also be characterized as having one or more functional groups such as cis-hydroxyl, hydroxyl, carboxyl, sulfate, sulfonate, amino or amide. Modified gums such as carboxyalkyl derivatives, e.g., carboxymethylguar and hydroxyalkyl derivatives, e.g., hydroxypropylguar can also be employed. Doubly derivatized gums such as carboxymethylhydroxypropylguar can also be used.

Modified celluloses and derivatives thereof can also be employed as gelling or viscosifying agents in accordance with the present invention. Examples of water-soluble cellulose ethers which can be used include, but are not limited to, carboxyethylcellulose, carboxymethylcellulose, carboxymethylhydroxyethylcellulose, hydroxyethylcellulose, methylhydroxypropyl-cellulose, methylcellulose, ethylcellulose, ethylcarboxymethylcellulose, methylethylcellulose, hydroxypropylmethylcellulose and the like. A particularly suitable derivatized cellulose is hydroxyethylcellulose grafted with vinyl phosphonic acid which is described in detail in U.S. Pat. No. 5,067,565 issued to Holtmyer et al. on Nov. 26, 1991, the disclosure of which is incorporated herein by reference thereto.

Of the galactomannans and derivative galactomannans, guar gum, hydroxypropylguar, carboxymethylhydroxypropylguar, hydroxyethylcellulose, carboxymethylhydroxyethylcellulose, carboxymethylcellulose, hydroxyethylcellulose grafted with vinyl phosphonic acid are preferred for use as gelling or viscosifying agents.

Various other gelling agents known to those skilled in the art including biopolymers such as xanthan gum, welan gum and succinoglycon can also be used. The gelling agent or agents utilized are included in the aqueous well treating fluids of this invention in an amount in the range of from about 0.125% to about 1.5% by weight of water in the treating fluid.

In order to further enhance the development of viscosity of the aqueous well treating fluid containing the above polysaccharide gelling agents, the gelling agents can be cross-linked by the addition of a cross-linking agent to the aqueous treating fluid. The cross-linking agent can comprise a borate releasing compound or any of the well known transition metal ions which are capable of creating a cross-linked structure with the particular gelling agent utilized. Preferred cross-linking agents for use with the above described gelling agents include, but are not limited to, borate releasing compounds, a source of titanium ions, a source of zirconium ions, a source of antimony ions and a source of aluminum ions.

When used, a cross-linking agent of the above types is included in the aqueous well treating fluid in an amount in the range of from about 0.1% to about 2% by weight of gelling agent in the treating fluid.

When the aqueous well treating fluid includes a gelling agent or a cross-linked gelling agent, a delayed breaker for the gelling agent or cross-linked gelling agent is included in the aqueous well treating fluid. That is, the delayed breaker is included in the aqueous treating fluid in an amount sufficient to effect a controlled reduction in the viscosity of the aqueous treating fluid after a desired period of time. Suitable delayed breakers which can be utilized include alkali metal and ammonium persulfates which are delayed by being encapsulated in a material which slowly releases the breaker. Such a material is precipitated particulate silica which is porous and remains dry and free flowing after absorbing an aqueous solution of the breaker. Precipitated silica can absorb chemical additive solutions in amounts up to about 400% by weight of the precipitated silica. The delayed release of a liquid chemical additive absorbed in a particulate porous precipitated silica is by osmosis whereby the encapsulated liquid chemical diffuses through the porous solid material as a result of it being at a higher concentration within the porous material than its concentration in the liquid fluid outside the porous material. In order to further delay the release of a liquid chemical additive, the porous precipitated silica can be coated with a slowly soluble coating. Examples of suitable such slowly soluble materials which can be used include, but are not limited to, EDPM rubber, polyvinyldichloride (PVDC), nylon, waxes, polyurethanes, cross-linked partially hydrolyzed acrylics and the like. A detailed description of the encapsulating techniques described above is set forth in U.S. Pat. No. 6,209,646 issued on Apr. 3, 2001 to Reddy et al., the disclosure of which is incorporated herein by reference thereto. Other delayed breakers which can be utilized include, but are not limited to, alkali metal chlorides and hypochlorites and calcium hypochlorites.

When used, a breaker of the above types is included in the aqueous well treating fluid in an amount in the range of from about 0.01% to about 5% by weight of water in the treating fluid.

As mentioned above, the polymer complex fluid loss control additives which are useful in accordance with the methods of the present invention are made by polymerizing a cationic, anionic or amphoteric polymer in the presence of a nonionic host polymer. The monomers which can be utilized in the polymerization of the cationic, anionic or amphoteric polymer are those that promote water solubility including, but not limited to, monomers such as 2-acrylamido-2-methylpropane sulfonic acid, 2-methacrylamido-2-methylpropane sulfonic acid, sulfonated styrene, vinyl sulfonic acid, allyl ether sulfonic acids such as propane sulfonic acid allyl ether, methallyl ether phenyl sulfonates, acrylic acid, methacrylic acid, maleic acid, itaconic acid, n-acrylamidopropyl-n,n-dimethyl amino acetic acid, n-methacrylamidopropyl-n,n-dimethyl amino acidic acid, n-acryloyloxyethyl-n,n-dimethyl amino acidic acid, n-methacryloyloxyethyl-n,n-dimethyl amino acidic acid, n-acryloyloxyethyl-n,n-dimethyl amino acidic acid, n-methacryloyloxyethyl-n,n-dimethyl amino acidic acid, crotonic acid, acrylamidoglycolic acid, methacrylamidoglycolic acid, 2-acrylamido-2-methylbutanoic acid and 2-methacrylamido-2-methylbutanoic acid. Nonionic monomers which can be used in the formed (synthesized, intercalated) polymer include, but are not limited to, $C_1$–$C_{22}$ straight or branched chain alkyl or aryl acrylamide, $C_1$–$C_{22}$ straight or branched chain n-alkyl or aryl methacrylamide, acrylamide, methacrylamide, n-vinylpyrrolidone, vinyl acetate, ethoxylated and propoxylated acrylate, ethoxylated and propoxylated methacrylate, hydroxy functional acrylates such as hydroxyethylacrylate and hydroxypropylacrylate, hydroxy functional methacrylates such as hydroxyethylmethacrylate and hydroxypropylmethacrylate, n,n-dimethylacrylamide, n,n-dimethylmethacrylamide, styrene, styrene derivatives and $C_1$–$C_{22}$ straight or branched chain alkyl, aryl or allyl ethers.

The polymer complexes of the present invention are formed by polymerizing one or more of the above described monomers in the presence of a nonionic host polymer. After preparation as described herein, the solution of polymer complex may be dried or otherwise separated from the reaction product and sold or used in substantially dry form. The host polymer can be a synthetic polymer, such as those produced by free radical polymerization or condensation polymerization or it can be a natural polymer such as a natural gum, a natural gum derivative, a starch, a modified starch, a cellulose, a cellulose derivative or an ethoxylated cellulose derivative. Other polymers that can be used include, but are not limited to, water-soluble vinyl polymers, polyolefins, polyacrylates, polyamides, polyesters, polyurethanes, xanthan gums, welan gums, succinoglycon, sodium alginates, galactomannans, carragenan, gum arabic, starch and its derivatives, guar ester derivatives, silicone containing polymers and their derivatives, polysiloxanes and their derivatives and proteins and their derivatives.

We may use the term "interjacent" to describe our polymer complexes. By interjacent, we mean that the polymers of the polymer complex are distributed homogeneously throughout the composition and intermingled to a degree that no visible phase separation will be observed after standing in the original solution for a long period of time. On the other hand, a three-dimensional network structure is also substantially absent (although there may be some branching), so that a solution manifests only a very minimal turbidity, if any. As a non-limiting example, an aqueous solution containing 5 percent by weight of a polymer or interjacent complex can be prepared and poured through a US Standard Sieve No. 100 (150 µm) and no particles are left on the screen. Alternatively, a 2.5% by weight solution of the polymer complexes or interjacent polymer complexes of the present invention will have a turbidity reading of less than 20 nephelometric turbidity units (NTU's). Solutions of the interjacent polymer complexes of our invention manifest no visible phase separation after standing at ambient conditions for three months.

Additional information concerning the uses of the polymer complex fluid loss control additives of this invention is included in U.S. Publication No. 2003/0083204 entitled "Methods of Treating Subterranean Zones Penetrated by Well Bores" filed on Apr. 15, 2002, the disclosure of which is incorporated herein by reference thereto. Also, additional information concerning the polymer complex fluid loss control agents of this invention is disclosed in Provisional Application Ser. No. 60/284,043 entitled "Water Soluble Polymer Complexes" filed on Apr. 16, 2001, the disclosure of which is incorporated herein by reference thereto. Additional information concerning the polymer complex compositions and their manufacture is disclosed in U.S. Publication No. 2002/0188040 titled "Water Soluble Polymer Complexes" filed Apr. 15, 2002, which is also incorporated herein completely by reference.

In order to further illustrate the methods of the present invention, the following examples are given.

EXAMPLE 1

A monomer mixture was prepared containing 0.0043 grams of methylene bis-acrylamide, 28.27 grams of 2-acrylamido-2-methylpropane sulfonic acid, 1.79 grams of acrylamide, 4.97 grams of ammonium chloride, 3.28 grams of N,N-dimethylacrylamide, 0.04 grams of the tetrasodium salt of ethylenediaminetetraacetic acid, 10.93 grams of a 50% sodium hydroxide solution, and 0.83 grams of a 50% aqueous solution of 2-mercaptoethanol. The mixture was added to a polymerization kettle containing 851.49 grams of deionized water. The pH of the resulting solution was above 8.5. The mixture was continuously agitated, heated to 118° F. and 0.67 grams of 2,2'-azobis(2-amidinopropane) hydrochloride initiator was added to the solution. 66.67 grams of hydroxyethylcellulose having 1.5 moles of ethylene oxide substitution were added to the agitated solution and the ethoxylated hydroxyethylcellulose was allowed to undergo complete hydration therein. A nitrogen sparge in the polymerization kettle was started and polymerization was allowed to proceed adiabatically. After a heat rise in the polymerization mixture stopped, the mixture was heated to 150° F. followed by the addition of 0.33 grams of 2,2'-azobis (2-amidinopropane) hydrochloride initiator dissolved in 1.33 grams of deionized water. The resulting solution was maintained at 150° F. for 30 minutes, allowed to cool and a 10% active solution of the polymer complex produced was collected.

The polymer complex produced consisted of 1 part by weight of the synthesized polymer containing 70 mole % of 2-acrylamido-2-methylpropane sulfonic acid, 17 mole % of N,N-dimethylacrylamide and 13 mole % of acrylamide, and 2 parts by weight of hydroxyethylcellulose having 1.5 moles of ethylene oxide substitution. This polymer complex was designated 2004-72.

Following the above described polymerization process, a different polymer complex was prepared consisting of 1 part by weight of a synthesized polymer containing 40 mole % of 2-acrylamido-2-methylpropane sulfonic acid, 30 mole % of acrylamide, 20 mole % of acrylic acid and 10 mole % of vinylpyrrolidone, and 1 part by weight hydroxyethylcellulose having 1.5 moles of ethylene oxide substitution. This polymer complex was designated 2004-96.

Following the same polymerization process described above, a synthesized polymer was prepared without the host polymer, i.e., hydroxyethylcellulose with 1.5 moles of ethylene oxide substitution. The synthesized polymer consisted of 40 mole % of 2-acrylamido-2-methylpropane sulfonic acid, 30 mole % of acrylamide, 20 mole % of acrylic acid and 10 mole % of vinylpyrrolidone. This synthetic polymer without the host polymer was designated 2004-97.

A cement slurry was prepared comprised of Lafarge Class H Portland cement, 30% of silica flour by weight of cement, 15% of fumed silica by weight of cement, 1% of a non-dispersing set retarder by weight of cement, 46.5% water by weight of cement and 2% of a mixture of foaming and foam stabilizing surfactants by volume of the water. The non-dispersing set retarder was comprised of a mixture of lignosulfonate, sugar acid and sulfonated lignin. The set retarder is described in detail in U.S. Pat. No. 6,227,294 B1 issued to Chatterji et al. on May 8, 2001, the disclosure of which is incorporated herein by reference thereto. The mixture of foaming and foam stabilizing surfactant was comprised of an ethoxylated alcohol ether sulfate surfactant, an alkyl or alkene amidopropylbetaine surfactant and an alkyl or alkene amidopropyldimethylamine oxide surfactant. The density of the cement slurry was 16.1 pounds per gallon. The three fluid loss control additives designated as 2004-72, 2004-96 and 2004-97 were added to separate portions of the above described cement slurry in the amounts given in Table I below. Thereafter, the test cement slurries were foamed and then tested for fluid loss in accordance with the API Specification For Materials And Testing For Well Cements referred to above using a Multiple Analysis Cement Slurry Analyzer (MACS). The MACS analyzer includes a sealable chamber having a known volume where a cement slurry is sheared at high energy while being pressurized and heated. The test cement slurries containing the fluid loss control additives were each placed in a standard 2-liter Waring blender. The weight of each of the cement slurries was 1,829.84 grams to which was added 10.69 grams of the mixture of foaming and foam stabilizing surfactants described above. After mixing in the Waring blender, each of the cement slurries was separately placed into the MACS chamber. The amount of each cement slurry utilized was predetermined to result in the desired foamed slurry density when the slurry was foamed sufficiently to completely fill the chamber of the MACS analyzer. After each cement slurry was placed in the MACS chamber, the chamber was sealed and the paddle inside the analyzer was rotated at approximately 1,000 RPM for 5 minutes with 1,000 psi nitrogen pressure applied to the cement slurry. As a result, the cement slurry in the chamber was converted to a test foamed cement composition having a density of 12 pounds per gallon. After being foamed, the test foamed cement composition was subjected to a temperature schedule which simulates well conditions while maintaining pressure on the foamed cement composition. After reaching the maximum temperature equivalent to the bottom hole circulating temperature (BHCT) of a well, the stirring of the test foamed cement composition was continued for 1 hour. The test foamed cement composition was then transferred through a special manifold system to a special fluid loss cell or to curing cells that were preheated and charged with nitrogen to the same pressure as the test foamed cement composition. By venting the nitrogen pressure from the fluid loss cell or curing cells, the test foamed cement composition was transferred from the analyzer chamber into the fluid loss cell or curing cells. When the test foamed cement composition was transferred to the fluid loss cell, the liquid effluents from the foamed cement composition were collected to determine the fluid loss control properties of the test foamed cement composition. The fluid loss test results are given in Table I below. In order to determine the stability of the test foamed cement composition, a portion of the test foamed cement composition was transferred to the curing cells. The cells were then subjected to the bottom hole static temperature (BHST) for curing. Upon the completion of curing, the nitrogen pressure was slowly released from the curing cells. The set foamed cement composition was then removed from the cells and tested for compressive strength. The results of these tests are also given in Table I below.

sition containing the polymer 2004-97 (without a host polymer) exhibited high fluid loss. All of the test foamed cement compositions were stable and had good compressive strengths.

EXAMPLE 2

A portion of the cement slurry designated 2004-72 was foamed in the MACS Analyzer as described in Example 1 above. The cement slurry was foamed to a density of 12 pounds per gallon at 80° F. and 1,000 psi. The temperature of the foamed cement composition was then gradually raised at a rate of 2.5° F. per minute to 250° F. and held at 250° F. for 1 hour. The foamed cement composition was then transferred to the curing cells which were preheated to 250° F. The curing cells were charged with nitrogen at 1,000 psi. The foamed cement composition in one cell had a density of 11.77 pounds per gallon and in the other cell 11.76 pounds per gallon before setting. The cells were then cured at 318° F. and 1,000 psi for 24 hours. The set foamed cement composition in the curing cells were removed therefrom and cooled to room temperature at ambient pressure. The set foamed cement compositions were each cut into 3 sections; top, middle and bottom and the average densities of the sections were determined. The results of these tests are given in Table II below.

TABLE II

Densities Of Set Samples

| Cell 1 Density, lb/gal | | | Cell 2 Density, lb/gal | | |
|---|---|---|---|---|---|
| Top | Middle | Bottom | Top | Middle | Bottom |
| 11.77 | 12.15 | 12.62 | 11.65 | 12.13 | 12.96 |

From Table II it can be seen that the average density of the top section was 11.71 pounds per gallon; the middle section was 12.14 pounds per gallon and the bottom section was

TABLE I

Fluid Loss And Compressive Strength Results

| Fluid Loss Control Additive Designation | Quantity of Fluid Loss Control Additive, % by wt. of cement | Fluid Loss, cc/30 min | | | Foam Stability at 12 lb/gal | Compressive Strength of Foam After Setting, psi |
|---|---|---|---|---|---|---|
| | | 160° F. | 250° F. | 275° F. | | |
| 2004-72 | 1.0 | 22 | — | — | Stable | 1134 |
| 2004-72 | 1.0 | 30 | — | — | | |
| 2004-72 | 1.5 | — | 24 | — | | |
| 2004-72 | 1.5 | — | — | 29 | | |
| 2004-96 | 1.0 | 16 | — | — | Stable | 503 |
| 2004-96 | 1.5 | — | 28 | — | | |
| 2004-96 | 1.5 | — | — | 32 | | |
| 2004-97 | 1.0 | 116 | — | — | Stable | 753 |

[1]Foamed fluid loss by MACS analyzer

From Table I it can be seen that the test foamed cement compositions containing the polymer complex fluid loss control additives 2004-72 and 2004-96 exhibited exceptional fluid loss control in the range of 100–275° F. bottom hole circulating temperatures (BHCT). The cement compo- 12.79 pounds per gallon. Thus, the density variation in the cured samples from top to bottom did not exceed 1 pound per gallon. This result indicates that the polymer complex fluid loss control additive utilized in accordance with this invention is non-dispersing.

EXAMPLE 3

Portions of the cement slurries described in Example 1 were foamed as described in Example 1 to densities of 12 pounds per gallon. The foamed cement compositions were tested for thickening times in accordance with the procedures set forth in the API Specification 10 referred to above. The results of the thickening time tests are set forth in Table III below.

TABLE III

Thickening Time Results

| Fluid Loss Control Additive Designation | Quantity of Fluid Loss Control Additive, % by wt. of Cement | Quantity of Silica Flour, % by wt. of Cement | Quantity of Fumed Silica, % by wt. of Cement | Quantity of Surfactants, % by wt. of Water | Temp., °F. | Thickening Time, hr:min |
|---|---|---|---|---|---|---|
| 2004-72 | 1.0 | 35 | — | — | 250 | 6:21 |
| 2004-72 | 1.0 | 30 | 15 | 1 | 250 | 4:24 |
| 2004-96 | 1.0 | 35 | — | — | 300 | 6:00+ |

From Table III it can be seen that the foamed cement compositions containing the polymer complex fluid loss control additive had good thickening times.

Thus, the present invention is well adapted to carry out the objects and attain the ends and advantages mentioned as well as those inherent therein. While numerous changes may be made by those skilled in the art, such changes are encompassed within the spirit of this invention as defined by the appended claims.

What is claimed is:

1. A dry residue of an aqueous solution comprising hydroxyethylcellulose and a polymer comprising monomer units derived from a sulfonic acid functional monomer, said solution characterized by (a) the substantial absence of visible separation of said hydroxyethylcellulose and said polymer after standing in solution under ambient conditions for three months and (b) a solubility reading of less than 20 nephelometric turbidity units when said solution has a concentration of 2.5 weight percent, wherein said polymer comprising monomer units derived from a sulfonic acid functional monomer comprises 25 mole percent to 75 mole percent units derived from 2-acrylamido-2-methyl propane sulfonic acid.

2. The residue of claim 1 wherein said polymer comprising monomer units derived from a sulfonic acid functional monomer comprises 40 mole percent to 70 mole percent units derived from 2-acrylamido-2-methyl propane sulfonic acid.

3. The residue of claim 1 wherein said hydroxyethylcellulose has 1 to 2 moles of ethylene oxide substitution and said polymer comprises, in molar ratios, 62–78 parts 2-acrylamido-2-methyl propane sulfonic acid:14–20 parts N,N-dimethylacrylamide:10–16 parts acrylamide.

4. The residue of claim 1 wherein said hydroxyethylcellulose has 1 to 2 moles of ethylene oxide substitution and said polymer comprises in molar ratios, 32–48 parts 2-acrylamido-2-methyl propane sulfonic acid:25–35 parts acrylamide:16–24 parts acrylic acid:7–13 parts vinyl pyrrolidone.

5. A polymer complex comprising a hydroxyethylated cellulose host polymer having 1.4–1.6 moles of ethylene oxide substitution and an intercalated water-soluble polymer comprising in molar ratios, 32–48 parts 2-acrylamido-2-methyl propane sulfonic acid:25–35 parts acrylamide:16–24 parts acrylic acid:7–13 parts vinyl pyrrolidone.

6. A well treating fluid comprising water, an interjacent polymer complex fluid loss control additive and (a) a hydraulic cement (b) a gas and a mixture of foaming and foam stabilizing surfactants in amounts sufficient to foam said well treating fluid, and optionally (c) a gelling agent, wherein said interjacent polymer complex fluid loss control additive comprises a host polymer and a water soluble polymer comprising 2-acrylamido-2-methyl propane sulfonic acid monomer units present in said polymer in an amount in the range of from about 25 mole percent to about 75 mole percent.

7. The well treating fluid of claim 6 wherein said interjacent polymer complex fluid loss control additive comprises hydroxyethylcellulose as the host polymer.

8. The well treating fluid of claim 6 wherein said gas comprises nitrogen.

9. The well treating fluid of claim 6 wherein said gelling agent is selected from the group consisting of guar gum, hydroxypropylguar, carboxymethylhydroxypropyl guar, hydroxyethylcellulose, carboxymethylhydroxyethylcellulose, carboxymethylcellulose, hydroxyethylcellulose grafted with vinyl phosphonic acid, xanthan gum, welan gum and succinoglycon, and wherein (c) includes a delayed gel breaker.

10. The well treating fluid of claim 6 wherein said gelling agent is present in said well treating fluid in an amount in the range of from about 0.125% to about 1.5% by weight of water in said treating fluid.

11. The well treating fluid of claim 7 wherein said hydroxyethylcellulose has 1–2 moles of ethylene oxide substitution.

12. The well treating fluid of claim 6 wherein said water soluble polymer comprising 2-acrylamido-2-methyl propane sulfonic acid comprises 2-acrylamido-2-methyl propane sulfonic acid monomer units present in said polymer in an amount in the range of from about 40 mole percent to about 70 mole percent.

13. The well treating fluid of claim 12 wherein the monomer units forming said polymer are further comprised of N,N-dimethylacrylamide monomer units present in said polymer in an amount in the range of from about 10 mole % to about 40 mole %.

14. The well treating fluid of claim 7 wherein said interjacent polymer complex fluid loss control additive is comprised of (a) a polymer comprising, in molar ratios, 62–78 2-acrylamido-2-methyl propane sulfonic acid:14–20 N,N-dimethylacrylamide:10–16 acrylamide and (b) a non-ionic polymer comprised of hydroxyethylcellulose having 1–2 moles of ethylene oxide substitution.

15. The well treating fluid of claim 7 wherein said interjacent polymer complex fluid loss control additive is comprised of a polymer comprising, in molar ratios, 32–48 2-acrylamido-2-methyl propane sulfonic acid:25–35 acrylamide:16–24 acrylic acid:7–13 vinyl pyrrolidone, and a nonionic polymer comprised of hydroxyethylcellulose having 1–2 moles of ethylene oxide substitution.

16. The well treating fluid of claim 12 wherein the monomer units forming said polymer are further comprised of vinyl pyrrolidone monomer units present in said polymer in an amount in the range of from about 5 mole percent to about 20 mole percent.

17. A method of making a polymer complex comprising polymerizing monomers including a sulfonic acid functional monomer in an aqueous medium in the presence of hydroxyethylcellulose having about 1 to about 2 moles of ethylene oxide substitution, said monomers and said hydroxyethylcellulose being present in said aqueous medium in a weight ratio of 1:10 to 10:1, wherein said sulfonic acid functional monomer is 2-acrylamido-2-methyl propane sulfonic acid and comprises 25 mole percent to 75 mole percent of said monomers.

18. Method of claim 17 wherein said polymer complex is an interjacent polymer complex in solution, said solution characterized by (a) the substantial absence of visible separation of said hydroxyethylcellulose and said polymer after standing in solution under ambient conditions for three months and (b) a solubility reading of less than 20 nephelometric turbidity units when said solution has a concentration of 2.5 weight percent.

19. A polymer complex comprising a hydroxyethylated cellulose host polymer having 1.4–1.6 moles of ethylene oxide substitution and an intercalated water-soluble polymer comprising, in molar ratios 62–78 parts 2-acrylamido-2-methyl propane sulfonic acid:14–20 parts N,N-dimethylacrylamide:10–16 parts acrylamide.

* * * * *